(12) United States Patent
Roberts et al.

(10) Patent No.: US 7,223,553 B2
(45) Date of Patent: May 29, 2007

(54) IMMUNOASSAYS FOR EVEROLIMUS

(76) Inventors: Mark Roberts, 14069 Plantation Wood La., Carmel, IN (US) 46033; Lili Arabshahi, 14157 Pepin Pl., Carmel, IN (US) 46032; Jared Boyd, 5155 Pin Oak Dr., Indianapolis, IN (US) 46254; Christopher T. Dennis, 13198 Lorenzo Blvd., Westfield, IN (US) 46074; Peter Marbach, 2 Raemelstrasse, Therwil (CH); George Aaron, 52 Brayton St., Englewood, NJ (US) 07631; Deng Hwang, 52 Tarryhill Rd., Tarrytown, NY (US) 10591; Alexei Boris Shvets, 210 Blairsden Ave., Carmel, IN (US) 46032

( * ) Notice: Subject to any disclaimer, the term of this patent is extended or adjusted under 35 U.S.C. 154(b) by 0 days.

(21) Appl. No.: 11/352,866

(22) Filed: Feb. 13, 2006

(65) Prior Publication Data
US 2006/0141548 A1    Jun. 29, 2006

Related U.S. Application Data

(62) Division of application No. 11/076,625, filed on Mar. 10, 2005, now abandoned.

(60) Provisional application No. 60/551,989, filed on Mar. 10, 2004.

(51) Int. Cl.
*G01N 33/53* (2006.01)
*G01N 33/532* (2006.01)
*G01N 33/533* (2006.01)
*C07K 16/00* (2006.01)
*C07K 1/00* (2006.01)
*C07K 1/13* (2006.01)

(52) U.S. Cl. ............... 435/7.93; 435/7.1; 435/810; 435/975; 436/544; 436/546; 436/56; 436/815; 530/388.9; 530/389.8; 530/402; 530/403; 530/405; 530/807; 540/456

(58) Field of Classification Search ............... 435/7.1, 435/961, 548, 975, 7.93, 810; 424/193.1; 540/456; 436/544, 546, 56, 815; 530/403, 530/405, 388.9, 389.8, 402, 807
See application file for complete search history.

(56) References Cited

U.S. PATENT DOCUMENTS 5,359,093 A * 10/1994 Adamczyk et al. ......... 549/223
6,328,970 B1 * 12/2001 Molnar-Kimber et al. ......... 424/184.1

FOREIGN PATENT DOCUMENTS

WO    WO 94/24304    * 10/1994

* cited by examiner

*Primary Examiner*—Long V. Le
*Assistant Examiner*—Shafiqul Haq
(74) *Attorney, Agent, or Firm*—Ice Miller LLP

(57) ABSTRACT

Immunoassays for the detection of everolimus are provided. Compounds for producing antibodies for everolimus, as well as antibodies produced therefrom, are also provided.

16 Claims, 9 Drawing Sheets

0.05 eq. Pd(PPh$_3$)$_4$
3 eq. Bu$_3$SnH
4 eq. AcOH
in CH$_2$Cl$_2$ at rt.

IMMUNOASSAYS FOR EVEROLIMUS

This application is a division of application Ser. No. 11/076,625, filed on Mar. 10, 2005 now abandoned, which claims priority to U.S. Provisional Application No. 60/551,989, filed Mar. 10, 2004, herein incorporated by reference.

FIELD OF INVENTION

The invention relates generally to reagents and methods for determination of everolimus in biological fluids.

BACKGROUND OF THE INVENTION

The everolimus [40-O-(2-hydroxyethyl)-rapamycin] is a novel macrolide immunosuppressant. Everolimus (also known as SDZ-RAD, RAD, Certican®) was developed by Novartis (Nashan B. The role of Certican in the many pathways of chronic rejection. Transplantation Proceedings, 2001, 33: 3215–3230, herein incorporated by reference) in an effort to improve upon rapamycin (Sirolimus), a proliferation signal inhibitor that blocks growth factor-driven transduction signals in the cellular responses to alloantigen (Cottens S, et al. O-Alkylated rapamycin derivatives and their use, particularly as immunosupressants. WO-009409010 28 Apr. 1994, herein incorporated by reference). Everolimus has greater stability and enhanced solubility in organic solvents, as well as more favorable pharmokinetics with fewer side effects than rapamycin (Sirolimus). Everolimus has been used in conjunction with microemulsion cyclosporin (Neoral®, Novartis) to increase the efficacy of the immunosuppressive regime (Kovarik J M, et al. Exposure-response relationship for Certican in de novo kidney transplantation: define a therapeutic range. Transplantation 2002; 73(6): 920–925, herein incorporated by reference).

The complexity of the clinical state, individual differences in sensitivity to immunosuppressive and nephrotoxic effects, has been rather challenging for physicians to balance between therapeutic efficacy and the occurrence of side effects (Wallemacq, Pierre E. Therapeutic monitoring of immunosuppressant drugs. Where are we? Clinical Chemistry and Laboratory Medicine (2004), 42 (11), 1204–1211, herein incorporated by Chemistry and Laboratory Medicine (2004), 42 (11), 1204–1211, herein incorporated by reference). Therapeutic drug monitoring (TDM), defined as the measurement and interpretation of concentration of these drugs in biological fluids, with as a final objective the prediction of organ responses, became an integral part of transplant protocols.

Therapeutic concentration of everolimus was reported (Kovarik et al.) as 3–15 ng/ml, which was consistent with efficacy while minimizing adverse effects in kidney transplantation. Recent data also showed that therapeutic drug monitoring (TDM) of everolimus would benefit heart transplant patients (Starling, Randall C.; et al. Therapeutic drug monitoring for everolimus in heart transplant recipients based on exposure-effect modeling. American Journal of Transplantation (2004), 4(12), 2126–2131, herein incorporated by reference). Everolimus trough levels were stable in the first year post-transplant and averaged 5.2±3.8 and 9.4±6.3 ng/mL in patients treated with 1.5 and 3 mg/day, respectively.

The TDM of everolimus was reported (McMahon L M, et al. High-throughput analysis of Certican (RAD001) and cyclosporin A (CsA) in whole blood by liquid chromatography/mass spectrometry using a semi-automated 96-well solid-phase extraction system. Rapid Comm. Mass Spectrometry 2000; 14: 1965–1971; Brignol N, et al. High-throughput semi-automated 96-well liquid/liquid extraction and liquid chromatography/mass spectrometric analysis of Certican (RAD001) and cyclosporin A (CsA) in whole blood. Rapid Communications in Mass Spectrometry 2002; 15: 1–10; Streit F. et al. Rapid liquid chromatography-tandem mass spectrometry routine method for simultaneous determination of sirolimus, Certican, tacrolimus, and cyclosporin A in whole blood. Clinical Chemistry. 2002; 48(6): 955–958, each of which herein incorporated by reference). However, methods that use HPLC, LC/MS can be impractical for commercial use due to, for example, long sample preparation time, long assay time, high cost, and labor-intensive procedures. For routine TDM of everolimus, the availability of simple automated tests and high throughput clinical analyzers is desirable.

SUMMARY OF THE INVENTION

The present invention is directed to novel derivatives of everolimus and novel everolimus immunogens. The present invention is also directed to polyclonal and monoclonal antibodies generated using everolimus immunogens, as well as labeled competitors and tracers. These antibodies, conjugates, and tracers are useful in immunoassays for the detection of everolimus in biological fluids.

In one aspect of the invention, competitive immunoassays for determining the presence of everolimus in a sample are provided. Illustrative competitive immunoassays comprise an antibody capable of specifically binding everolimus, and an everolimus compound conjugated to a detectable label, wherein the conjugated everolimus compound is configured to compete with the everolimus in the sample to bind with the antibody, and wherein the label provides a signal indicative of a concentration of everolimus in the sample when the everolimus in the sample is present in therapeutic drug monitoring concentrations. In one embodiment, the immunoassay is suitable for monitoring everolimus in the range of about 3 to about 15 ng/ml. In another embodiment, the competitive immunoassay provides a signal indicative of the concentration of everolimus over a broader range, illustratively from about 0 to about 40 ng/ml.

In another aspect of the invention, methods for determining the amount of everolimus in a sample are provided. The methods comprise mixing the sample with an antibody capable of specifically binding everolimus, and an everolimus compound conjugated to a detectable label, wherein the conjugated everolimus compound is configured to compete with the everolimus in the sample to bind with the antibody, measuring a signal from the detectable label indicative of a concentration of everolimus in the sample, and determining the amount of everolimus in the sample.

In yet another aspect of the invention, compounds are provided having the following structure

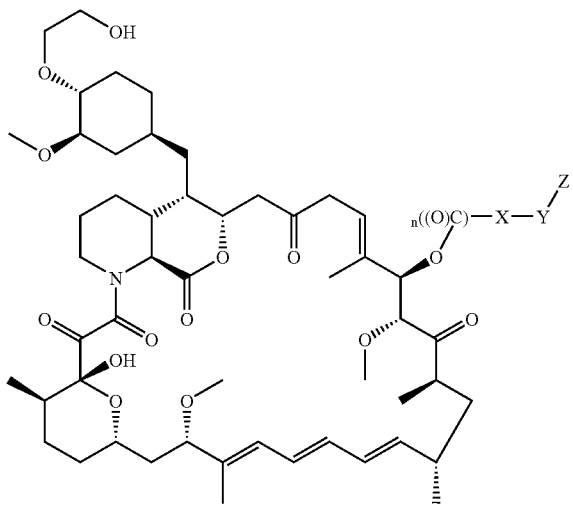

Formula II wherein n is 0 or 1;

X is a linker chain comprising 3–10 carbon or hetero atoms, wherein the linker chain may be substituted or unsubstituted and may be straight or branched;

Y is selected from the group consisting of —C(O)—, —NH—, —S—, —CH$_2$— and —O—; and Z is an antigenic carrier or a label.

In one particular illustrative embodiment, X is —CH$_2$—CH$_2$—CH$_2$—CH$_2$—CH$_2$—, Y is —C(O)—, and Z is the antigenic carrier. Antibodies produced using such compounds and immunoassay kits using the antibodies are also provided.

Additional features of the present invention will become apparent to those skilled in the art upon consideration of the following detailed description of preferred embodiments exemplifying the best mode of carrying out the invention as presently perceived.

DETAILED DESCRIPTION OF THE INVENTION

Figure 1:
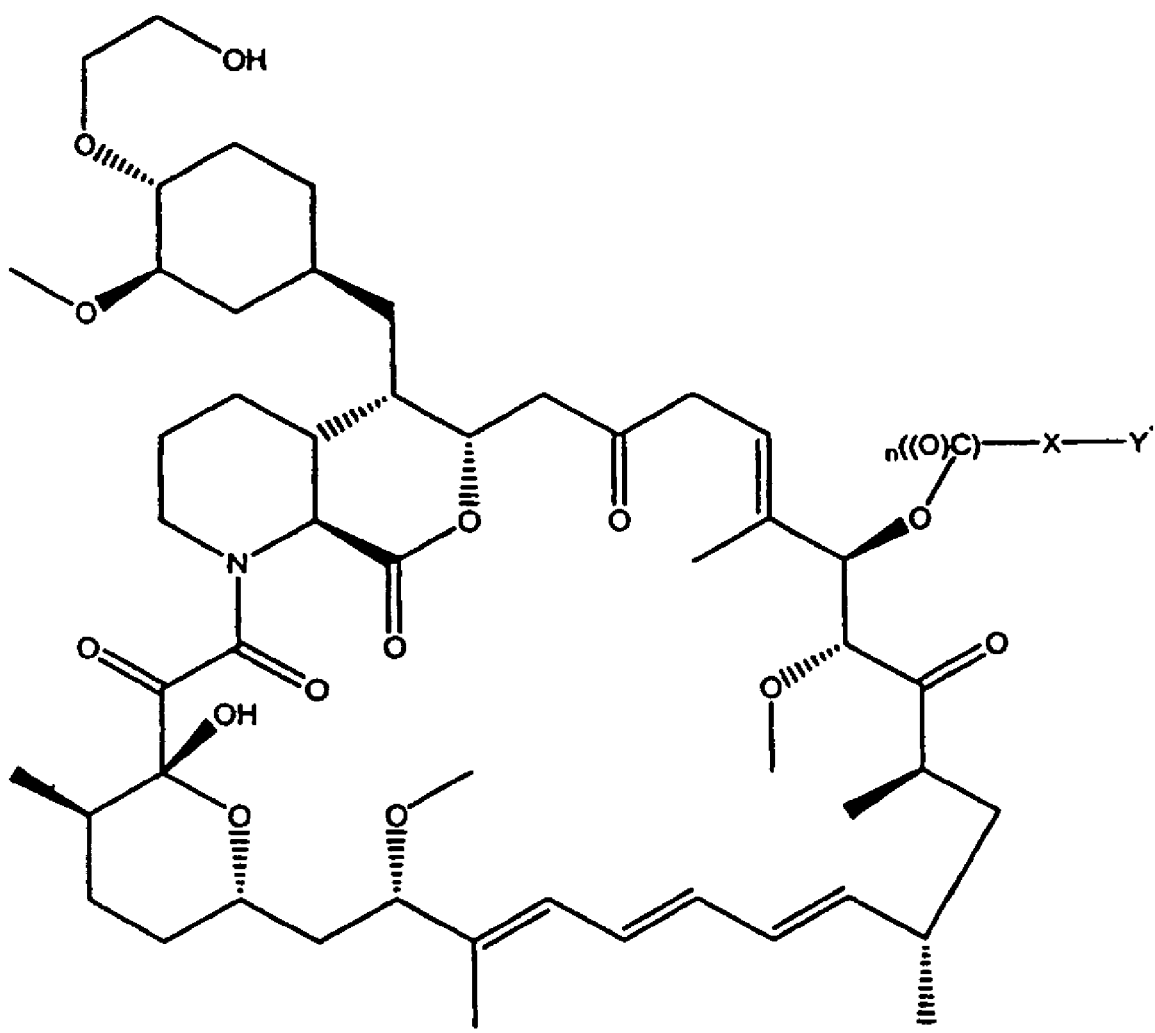
FIG. 1 shows the structure of an illustrative everolimus derivative of the present invention.

"Everolimus" is an immunosuppressive drug, sold by Novartis AG under the trademark CERTICAN®. Everolimus has the structure of Formula I:

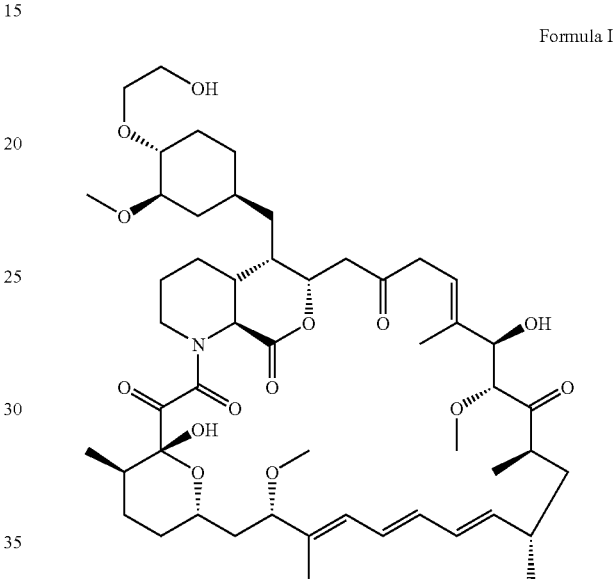

Formula I

"Haptens" are partial or incompletes antigens. They are usually protein-free substances, mostly of low molecular weight, which are not generally capable of stimulating antibody formation, but which do react with antibodies. Antibodies may be formed by coupling a hapten to a high molecular weight antigenic carrier and then injecting this coupled product, i.e., immunogen, into a human or animal subject. Everolimus is a hapten.

The phrase "antibody capable of specifically binding everolimus" as used herein refers to an antibody with the capacity to react with at least one epitope within the drug in a true antibody-antigen reaction, as opposed to non-specific interaction.

The term "analog" or "derivative" refers to a chemical compound or molecule made from a parent compound or molecule by one or more chemical reactions.

An "activated hapten" refers to a hapten derivative that has been provided with an available site for reaction, such as by the attachment of a linking group, for synthesizing a hapten derivative conjugate.

As used herein, a "linking group" or "linker" refers to a portion of a chemical structure that connects two or more substructures such as haptens, carriers, immunogens, labels, tracers, or other linkers. A linking group has at least one uninterrupted chain of atoms other than hydrogen (or other monovalent atoms) extending between the substructures. The atoms of a linking group and the atoms of a chain within a linking group are themselves connected by chemical bonds. Linkers maybe straight or branched, saturated or unsaturated carbon chains. They may also include one or more heteroatoms within the chain or at termini of the chains. By "heteroatoms" it is meant atoms other than carbon atoms, illustratively oxygen, nitrogen, sulfur, and phosphorus. The linking group may also include cyclic or aromatic groups as part of the chain or as a substitution on one of the atoms in the chain. The number of atoms in a linking group or linker is determined by counting the atoms other than hydrogen. The number of atoms in a chain within a linking group is determined by counting the number of atoms other than hydrogen along the shortest route between the substructures being connected. Linking groups may be used to activate a hapten, e.g. provide an available site on a hapten for synthesizing a conjugate of a hapten with a label or carrier.

The terms "immunogen" and "immunogenic" as used herein refer to substances capable of producing or generating an immune response in an organism.

An "active ester" refers to an ester group that can react with a free amino group of compound such as, for example, peptides and proteins. Examples of active esters include N-hydroxysuccinimide, p-nitrophenyl, pentafluorophenyl, and N-hydroxybenzotriazolyl.

A "carrier" or "immunogenic carrier," as the terms are used herein, is an immunogentic substance, commonly a protein, that can join with a hapten, thereby enabling the hapten to induce an immune response and elicit the production of antibodies that can bind specifically with the antigen (hapten). Carrier substances include proteins, glycoproteins, complex polysaccharides, particles, and nucleic acid that are recognized as foreign and thereby elicit an immunologic response from the host. Various proteins may be employed as a poly (amino acid) immunogenic carrier. These proteins include albumins and serum proteins, e.g., globulins, ocular lens proteins, lipoproteins, etc. Illustrative proteins include bovine serum albumin (BSA), keyhole limpet hemocyanin (KLH), egg ovalbumin, bovine gamma-globulin (BGG), etc. Alternatively, synthetic poly (amino acids) may be used. The immunogenic carrier can also be a polysaccharide, which is a high molecular weight polymer built up by repeated condensations of monosaccharides. Examples of polysaccharides are starches, glycogen, cellulose, carbohydrate gums such as gum arabic, agar, and so forth. The polysaccharide can also contain poly (amino acid) residues and/or lipid residues. The immunogenic carrier can also be a poly (nucleic acid) either alone or conjugate to one of the poly (amino acid)s or polysaccharides mentioned above. The immunogenic carrier can also be a particle. The particles are illustratively at least about 0.02 microns (μm) and illustratively not more than about 100 μm, and usually about 0.05 μm to 10 μm in diameter. The particle can be organic or inorganic, swellable or non-swellable, porous or non-porous, optionally of a density approximating water, generally from about 0.5 to 1.5 g/ml, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly (amino acid)" or "polypeptide" is a polyamide formed from amino acids. Poly (amino acid)s will illustratively range from about 2,000 molecular weight, having no upper molecular weight limit, normally being less than 10,000,000 and optionally not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain. The terms "peptide", "polypeptide", and "poly (amino acid)" are used synonymously herein to refer to this class of compounds without restriction as to size. Larger members of this class are also referred to as proteins.

A "label", "detector molecule", or "tracer" is any molecule that produces, or can be induced to produce, a detectable signal. The label can be conjugated to an analyte, an immunogen, an antibody, illustratively the antibody produced in response to the antigenic compound or a secondary antibody having specificity therefor, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, and hapten radioactive isotopes.

The term "antigenic compound" as used herein is a compound used to produce an immune response. Illustratively, the antigenic compound is a hapten, for example everolimus, linked to an immunogenic carrier. The antigenic compound is used to generate the desired antibodies.

The term "labeled competitor" as used herein is a molecule capable of specific binding to antibodies having specificity for everolimus, wherein the molecule is linked to a detectable label or tracer. Illustratively, the molecule is everolimus or a derivative or analyte thereof.

The term "biological sample" includes, but not limited to, any quantity of a substance from a living thing or formerly living thing. Such living things include, but are not limited to, humans, mice, monkeys, rats, rabbits, horses, and other animals. Such substance include, but are not limited to, blood, serum, urine, tears, cells, organs, tissues, bone, bone marrow, lymph, lymph nodes, synovial tissue, chondrocytes, synovial macrophages, endothelial cells, and skin.

The term "therapeutic drug monitoring concentrations" refers to concentrations of the drug from that which provides no effect up to that of toxic effect. For everolimus, as is currently understood, the therapeutic range is generally 3–15 ng/ml. However, it is understood that it may be useful to provide information across a broader range, and the assay range is generally broader than the therapeutic range. Accordingly, assays that monitor therapeutic drug monitoring concentrations may provide sensitivity across a broader range of everolimus concentrations.

The term "patient" includes human and animal subjects.

Numerous quantitative immunoassay formats for detecting a hapten such as a drug or other small molecule in a body fluid are known. An assay method for everolimus illustratively includes combining the sample with an anti-everolimus antibody and detecting the amount of the anti-everolimus antibody-everolimus complex, as indicative of the amount of everolimus in the sample.

Illustrative immunoassays employ polyclonal antibodies and/or monoclonal antibodies with appropriate sensitivity and specificity to everolimus to provide information about everolimus concentrations statistically comparable to that obtained through analytical methods such as LC/MS. Such immunoassays illustratively are useful in monitoring levels of the drug in patient samples.

Designing an immunoassay for the detection of a small molecule such as a drug can be a challenge. Such small molecules often lack antigenicity, making it difficult to generate antibodies. This is particularly problematic with drugs such as everolimus, which suppress the immune response. To increase the immunogenicity, larger antigenic compounds, illustratively proteins or polypeptides, including but not limited to bovine serum albumin, ovalbumin, keyhole limpet hemocyanin, and the like, are conjugated to the drug. Further, detection of the drug in an immunoassay generally requires the use of a detectable label conjugated to an antibody, an analyte, or analyte analog.

Immunogens may be made by coupling everolimus to an antigenic carrier protein through a linker reacted with one of the hydroxy groups, illustratively the hydroxyl at position 28. Such methods are described in U.S. Pat. No. 6,635,745 and European Patent No. EP 0 693 132, herein incorporated by reference. However, it has been found that an extended linker between the antigenic carrier leads to the production of more sensitive antibodies. Without being bound to any particular theory, presumably, the longer linker provides for a more accessible epitope, resulting in increased specificity of the antibody for everolimus.

In one illustrative example, the immunogenic conjugate is illustratively a compound shown in FIG. 1 and in Formula II below:

Formula II

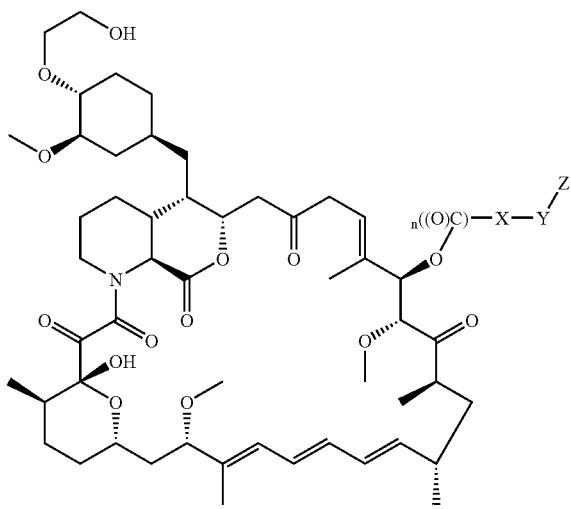

wherein
  n is 0 or 1;
  X is a linker chain comprising 3–10 carbon or hetero atoms, wherein the linker chain may be substituted or unsubstituted and may be straight or branched;
  Y is selected from the group consisting of carbonyl, —NH—, —S—, —CH$_2$— and —O—; and
  Z is an antigenic carrier.

In this embodiment, the linker (X) comprises a chain of three or more atoms, wherein at least one atom is carbon (C). The linker molecule can be a straight or branched chain and, in additional to at least one C atom, can contain heteroatoms such as N, O, S, and P, which can be substituted independently of one another. The linker can also contain multiple bonds. If the linker is branched, the branches may form rings. When the linker is branched, the length of the linker is determined by the number of atoms in the shortest path between the everolimus and the conjugate. Illustratively, the linker (X) comprises a chain of between three and ten atoms, more illustratively between four and seven atoms, and even more illustratively four to five atoms. In one particularly well suited example, the linker comprises a chain of five atoms. It is understood that antigenic compounds or other everolimus conjugates can be made by coupling through other positions on the everolimus molecule, illustratively one of the ketone groups at positions 26, 32, or 9, by way of suitable linkage (e.g. oxime, hydrazone), wherein the linker has sufficient length to provide access to a suitable everolimus epitope, while not providing too much separation between the everolimus and the antigenic carrier. The linker may be appended to a suitable functional group that permits coupling to a protein or other biomolecule, or to a solid support surface.

Figure 6:
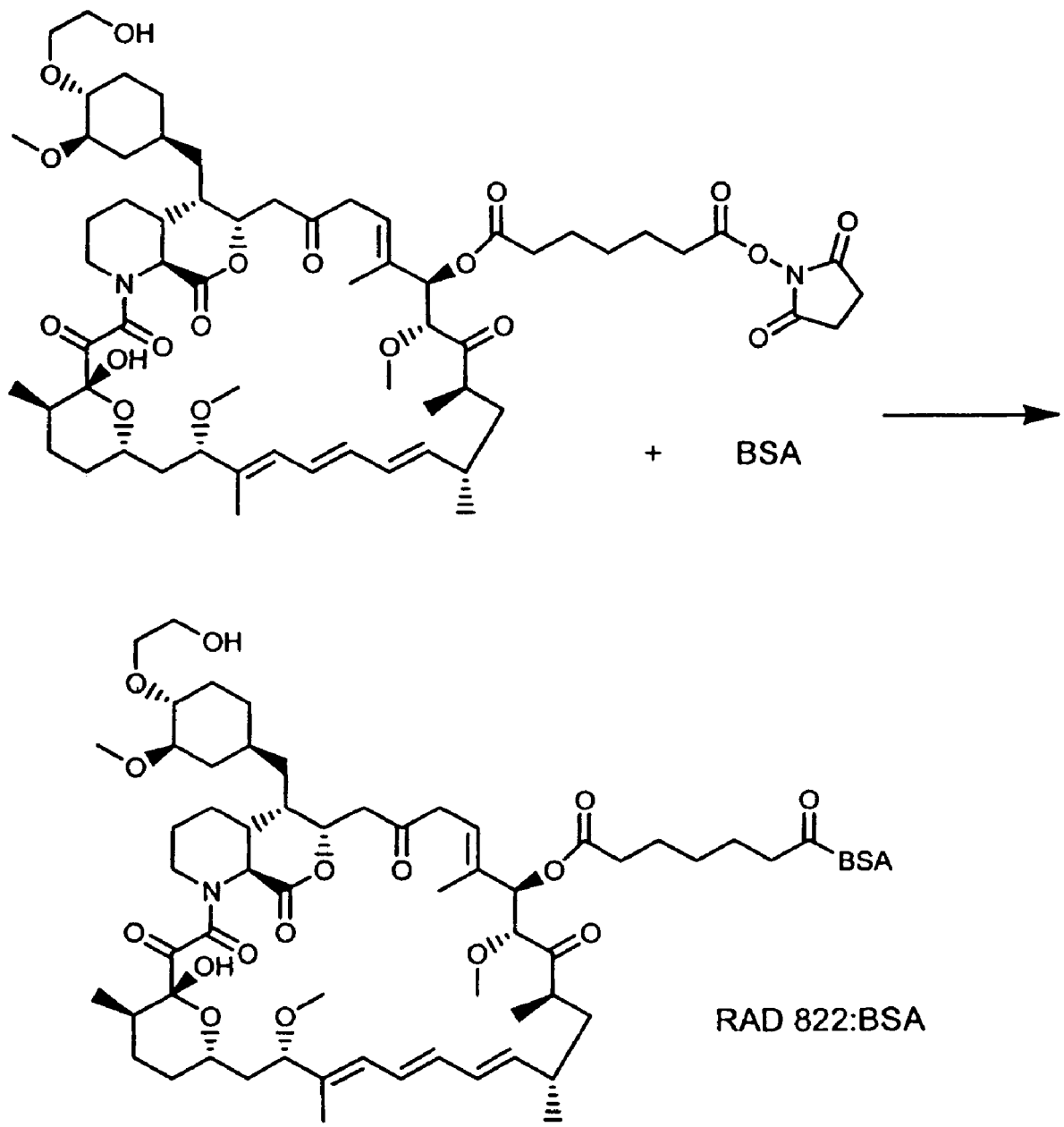
FIG. 6 shows synthesis of RAD 822: BSA immunogen.
Figure 9:
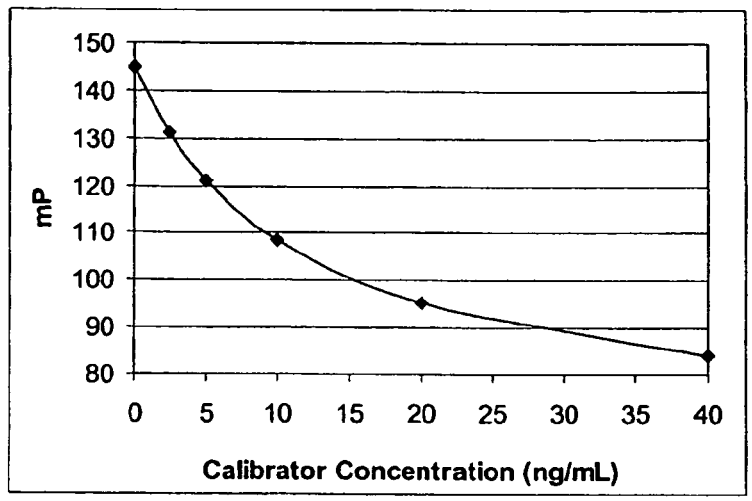
FIG. 9 shows a calibration curve (FPIA) X axis-calibrator values, Y axis-rates (mp) antibody (polyclonal), FP tracer (RAD822:FAMCO-E)

In one particular example, n=1, X is a chain of 5 atoms, and Y is —C(O)—. An example of such an immunogenic compound is RAD 822:BSA, as shown in FIG. 6, wherein Z is BSA. Antibodies produced using RAD 822:BSA have proven to demonstrate strong binding (>100 mP) and strong inhibition (>50% @ 50 ng/mL), as shown in the calibration curve of FIG. 9. Another such example wherein strong binding and strong inhibition is expected is antibodies produced using an immunogenic compound of Formula II wherein n=1, X is a chain of 7 atoms (for example —(CH$_2$)$_7$—), and Y is —C(O)—. It is expected that antibodies produced using other compounds of Formula II will also demonstrate strong binding and strong inhibition. It is understood, however, that medium binding (50–100 mP and/or medium inhibition (50% at 50–500 ng/mL) may be acceptable for some embodiments. The antibodies generated from the compounds of Formula II are well suited for competitive and non-competitive assays.

The immunogenic conjugate is useful for generation of polyclonal as well as monoclonal antibodies. Depending upon the purpose of the detection system, antibodies may be selected to target everolimus with little or no cross-reactivity to metabolites, or, alternatively, antibodies with the capacity to recognize one or more of the metabolites and/or related drugs as well as everolimus can be selected. A comprehensive study of the biotransformation of everolimus by human liver microsomes has identified at least 11 metabolites resulting from hydroxylation and demethylation of everolimus (Bornsen K O, et al. Electrospray ionization and collisionally induced dissociation of RAD001 and related compounds and structural characterization of RAD001 metabolites by nano-spray and micro liquid chromatography mass spectrometry, Jacobson W, et al. Comparison of the in vitro metabolism of the macrolide immunosuppressants sirolimu and RAD. Transplantation Proceedings 2001; 33: 614–615, herein incorporated by reference), with the major metabolites being hydroxyl-(24/25 OH RAD, 46 OH RAD), ring-open compounds (RAD SA, RAD PSA), and 40-phosphatidylcholine-RAD (RAD PC). The generation of everolimus metabolites is attributed to cytochrome P450 3A4, the most abundant of the CYP enzymes in the liver and intestine, also involved in Cyclosporin (CsA) and rapamycin metabolism. Illustratively, if antibodies capable of distinguishing everolimus from metabolites are desired, antibodies optionally may be induced by immunogens made from 28-O-derivatives.

Besides immunogens, other everolimus conjugates may be prepared. When the linkage via the 28-O-position is used to produce a labeled competitor molecule, Z of Formula II may be biotin, horseradish peroxidase or other enzymes, fluorescent labels, and dyes, or particles such as metal sols, latex particles, polystyrene particles and the like, or any other label, detector molecule, or tracer, as discussed above. Such conjugates are formed by any number of routine procedures well known to those skilled in the art. It is possible to prepare conjugates of everolimus that are useful for a variety of immunoassays, including but not limited to fluorescence polarization immunoassay, cloned enzyme donor immunoassay, lateral flow immunoassays, chemiluminescence microparticle assays and immunoturbidimetric assays. Several embodiments are described herein.

Figure 5:
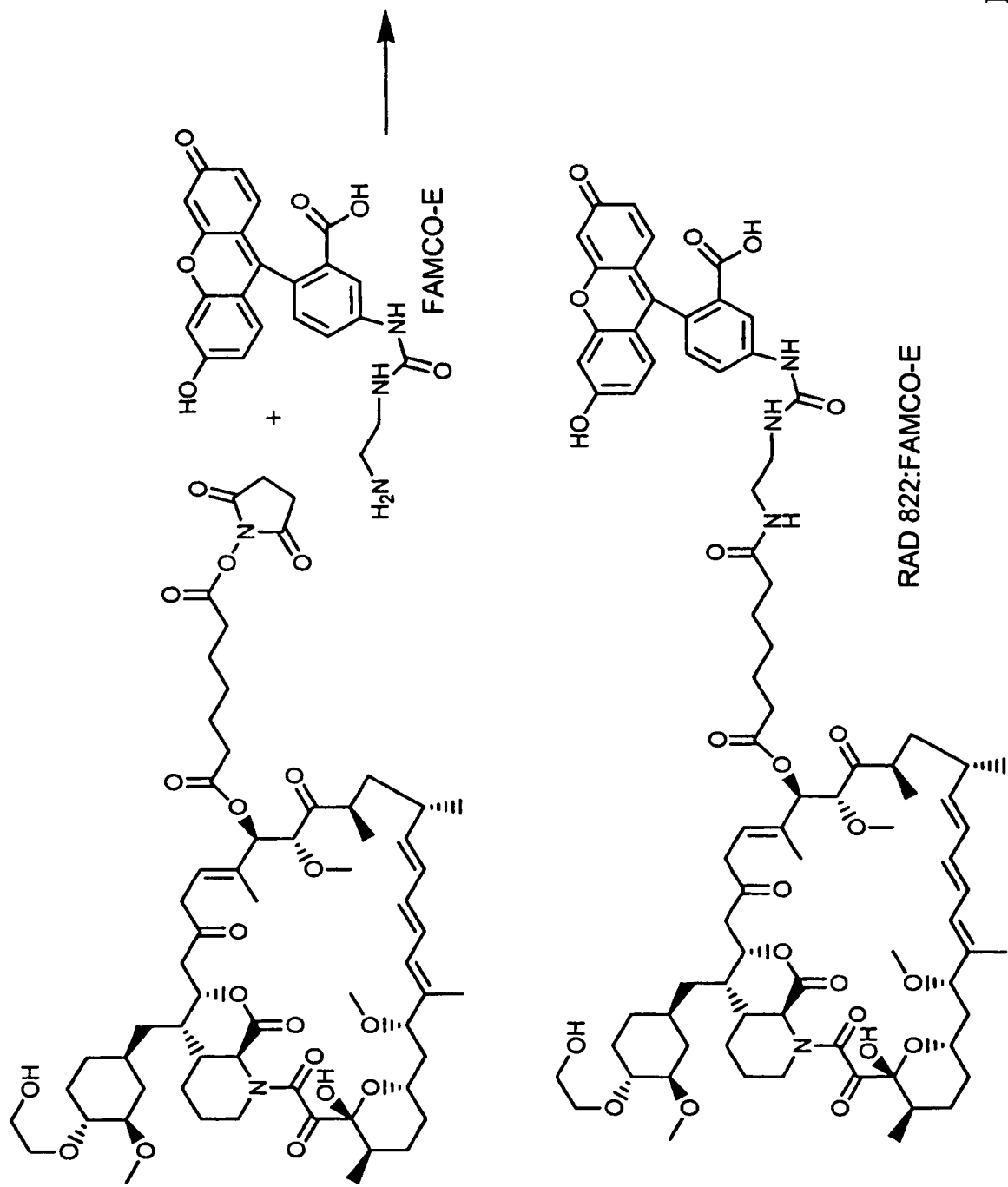
FIG. 5 shows synthesis of RAD 822: FAMCO-E FP tracer.

In one illustrative embodiment, antibodies are produced using an antigenic compound of Formula I, for example RAD 822:BSA, as shown in FIG. 6. In one competitive assay, the labeled competitor may be derived from everolimus using a linkage that is the same as or similar to that of the antigenic compound, for example RAD 822:FAMCO-E, as shown in FIG. 5. However, it is understood that when the labeled competitor is a 28-O-derivative of everolimus, the linker chain, as represented by X in Formula II, is not limited to a chain comprising 3–10 atoms. In some competitive assays, it is desirable to have a labeled competitor that binds to the antibody with less specificity than everolimus binds to the antibody, allowing the labeled competitor to be displaced more readily in the presence of everolimus. Accordingly, shorter linkers may be desirable, to limit access of the antibody binding sites and to weaken specific binding with the antibody. Linkers longer than 10 atoms may be useful as well, as the distance between the label and the everolimus is not critical in many embodiments. Thus, it is understood that the linker of the labeled competitor is not limited to the definition of X in Formula II.

In another example, the labeled competitor is derived from everolimus using a different linkage. One suitable labeled competitor, as shown in Formula III:

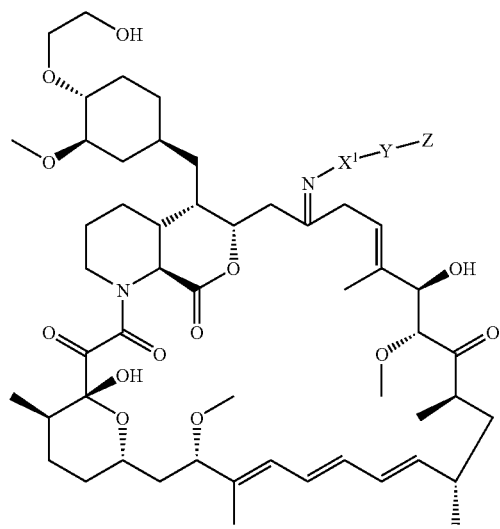

Formula III wherein $X^1$ is a linker chain comprising one or more atoms, each of which may be substituted or unsubstituted and may be branched or unbranched;

Y is defined as above; and

Z is a label, as defined above.

For a labeled competitor, the structure of the linker $X^1$ may be chosen based on the particular assay. As discussed above, it may be desirable to provide a short linker having only one or two atoms in the chain (illustratively —O—$CH_2$—), to reduce specific binding to the antibody. On the other hand, it may be desirable to provide a long linker, illustratively when the everolimus of the labeled competitor is being tethered to a solid support, and additional flexibility in the linker chain is desired. The longer linker may comprise a chain of any length, illustratively from 10 to 100 atoms. Further, it is understood that a linker as defined as X above, is suitable in many applications. Still further, it is understood that compounds of Formula III, wherein $X^1$ is X, as defined above for Formula II;

Y is defined as above Formula II; and

Z is an antigenic carrier, are suitable antigenic compounds for producing antibodies for everolimus.

Figure 7:
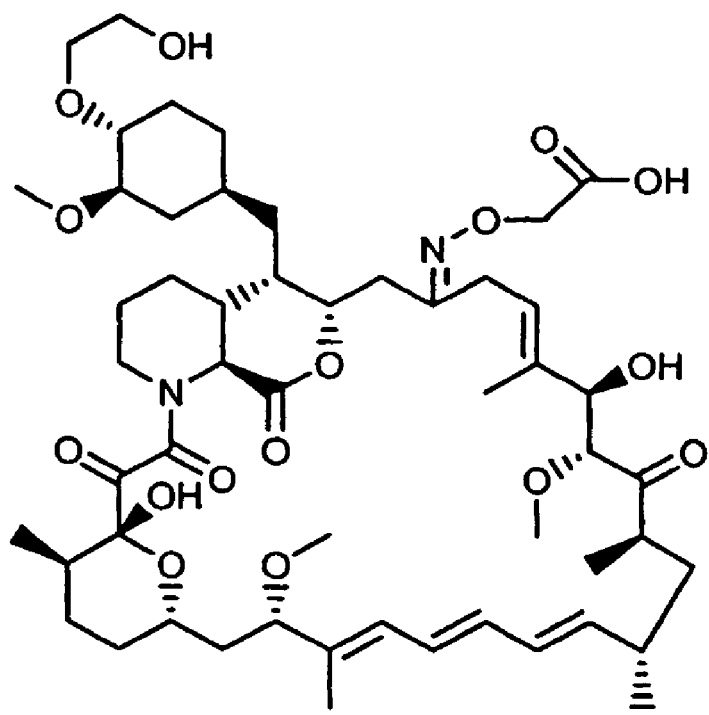
FIG. 7 shows the structure of a 32-oxime derivative of everolimus.

One illustrative competitive assay uses antibodies produced using an antigenic compound of Formula II, illustratively RAD 822:BSA, as shown in FIG. 6, and a labeled competitor of Formula III, illustratively the 32-oxime compound shown in FIG. 7, wherein the succinimide is replaced with a suitable label for a competitive immunoassay. For FPIA, the label may be FAMCO-E, although other suitable labels or tracers may be used. Since the unbound drug-everolimus has higher affinity for the antibody (produced from RAD 822:BSA immunogen) than the labeled 32-oxime derivative, a very small quantity of unbound everolimus in a sample should have detectable effect on the rate of agglutination governed by the bound oxime derivative. Thus, if the labeled 32-oxime derivative is, for example, immobilized on latex, a high sensitivity (required for detection of everolimus due to the extremely low and narrow therapeutic range-3–15 ng/ml) can be achieved.

Oxime linkages are more stable to hydrolytic cleavage than ester bonds. In addition, it has been found that the oxime derivative (position 32) will not undergo an elimination reaction in most useful conditions. The oxime derivate (activated ester) would be a desirable candidate in various assays, including latex enhanced immunoturbidimetric assays. Micro-particles coupled the oxime derivative have showed improved stability.

It is understood that any combination of antibodies produced using the above-described antigenic compounds and the above-described labeled competitors may be used in competitive assays, the choice of which depend on the specific assay and desired sensitivity.

Fluorescence Polarization Immunoassay for Everolimus

Fluorescence polarization immunoassay (FPIA) technology is based upon competitive binding between an antigen/drug in a sample and a known concentration of labeled antigen/drug. FPIA is described in U.S. Pat. No. 4,593,089, incorporated herein in its entirety. In the assay system, the sample antigen, such as everolimus, competes with fluorescein-labeled antigen or antigen-analog for a fixed number of antibody sites. The main components of the FPIA system are: i) antibody capable of specifically binding to the antigen/drug, ii) the sample suspected of containing the antigen/drug, and iii) the antigen/drug or analog labeled with fluorescein. Because of the rotational properties of molecules in solution, the degree of polarization is directly proportional to the size of the molecule. Polarization increases as molecular size increases. When linearly polarized light is used to excite the fluorescein-labeled antigen/drug, which is small and rotates rapidly in solution, emitted light is significantly depolarized. When fluorescein-labeled antigen/drug is bound to antibody, rotation is slowed and emitted light is highly polarized. Increased amounts of unlabeled antigen/drug in the sample will result in decreased binding of fluorescein-labeled antigen/drug by antibody, and decreased polarization of emitted light from sample. In the present examples, the precise relationship between polarization and concentration of the unlabeled everolimus in the sample is established by measuring the polarization values of calibrators with known concentration of everolimus.

Homogeneous Microparticle (Immunoturbidimetric) Immunoassay for Everolimus Format A:

In one embodiment, a kit is provided with a liquid reagent set used for performing immunoturbidimetric assays for the measurement of everolimus concentrations in whole blood, blood hemolysate, serum or plasma. In this technology, an everolimus conjugate, illustratively a 28-O-activated everolimus conjugate, is loaded on a microparticle, for example, any of the microparticles manufactured and/or sold by Seradyn, Inc. (Indianapolis, Ind.), including, but limited to, polystyrene or carboxylate-modified polystyrene and streptavidin-coated magnetic particles. Antibody capable of specifically binding everolimus is formulated in a standard buffer system. A competitive reaction takes place between everolimus immobilized on the microparticles and everolimus in the patient's sample for binding to a limited amount of anti-everolimus antibody in the reaction solution. Agglutination of particles is inhibited by the presence of drug in patient sample.

Format B:

This embodiment is similar to that described above as Format A except that an antibody capable of specifically binding everolimus is loaded on the microparticle. A derivative of everolimus, illustratively 28-O-activated everolimus, is linked to a macromolecule of choice, for example, bovine serum albumin, ovalbumin, dextran, and the like, to form a drug conjugate. A competitive reaction takes place between the drug conjugate in buffered solution and everolimus in the patient's sample for binding to anti-everolimus antibody immobilized on the microparticles. Agglutination of particles is inhibited by the presence of drug in patient sample.

Cloned Enzyme Donor Immunoassay—CEDIA® Technology for Everolimus

CEDIA® (trademark of Roche) has proven to be a highly accurate method for quantitation of therapeutic drugs. CEDIA® is the subject of several patents including U.S. Pat. No. 4,708,929, claiming competitive homogeneous assay methods, U.S. Pat. No. 5,120,653, claiming a recombinant DNA sequence for coding the enzyme donor fragment and a host for such a vector, U.S. Pat. No. 5,604,091, claiming amino acid sequences of the enzyme donor fragment, and U.S. Pat. No. 5,643,734, teaching kits for CEDIA® assays. All of the above patents are herein incorporated by reference in their entirety. CEDIA is based upon the competition of a drug in the biological sample with drug conjugated to the inactive genetically-engineered enzyme-donor (ED) fragment from $\beta$-D-galactoside galactohydrolase (E.C. 3.2.1.23) or $\beta$-galactosidase ($\beta$gal) from $E.\ coli$ for binding to an antibody capable of specifically binding the target drug. If the target drug is present in the sample, it binds to the antibody, leaving the ED portion of the ED-drug conjugate free to restore enzyme activity upon association with enzyme acceptor (EA) fragments, also from $\beta$-D-galactoside galactohydrolase (E.C. 3.2.1.23) or $\beta$-galactosidase ($\beta$ gal) from $E.\ coli$, in the assay reaction mixture. The active enzyme is then capable of producing a quantifiable reaction product when exposed to appropriate substrate. An illustrative substrate is chlorophenol red-$\beta$-D-galactopyranoside (CPRG), cleaved by the active enzyme into galactose and CPR. CPR is measured by absorbency at wavelength 570 nm. If drug is not present in the sample, the antibody binds to the ED-drug conjugate, inhibiting association of the ED fragments with the EA fragments, thus inhibiting restoration of enzyme activity. The amount of reaction product and resultant absorbance change are proportional to the amount of drug in the sample.

Chemiluminescence Heterogeneous Immunoassay

In one embodiment, a competitive assay using chemiluminescence microparticle immunoassay (CMIA) technology comprises use of antibodies, capable of specifically binding to everolimus, coupled to particles, in particular magnetic particles or particles suitable for separation by filtration, sedimentation or other means. A label comprising everolimus linked to a suitable chemiluminescent molecule, for example an acridinium ester, competes with free everolimus in the patient's sample for the limited amount of anti-everolimus antibody on the magnetic particle. After a routine wash step to remove unbound label, the amount of chemiluminescence, expressed in Relative Light Units (RLU), is measured. The amount of chemiluminescence is inversely related to the amount of free drug in the patient's sample and concentration is determined by constructing a standard curve using known values of the drug.

Other Immunoassay Formats

The derivatives, antibodies, immunogens, and/or other conjugates described herein are also suitable for use with any of a number of other homogeneous and heterogeneous immunoassays with a range of detection systems. The examples presented herein are not intended to be limiting.

Thus, the present invention provides everolimus derivatives that are useful for the preparation of immunogens and conjugates for use in immunoassays for the detection of everolimus. By coupling an everolimus analog according to the present invention to an immunogentic carrier material, polyclonal or monoclonal antibodies can be produced and isolated, which are useful reagents for immunoassays for the detection of everolimus.

Coupling can be accomplished by any chemical reaction that will bind the label or carrier. This linkage can be accomplished by a variety of chemical mechanisms, for instance covalent binding, affinity binding, intercalation, coordinate binding, and complexation. Most often the linkage is made through covalent bonding. Covalent binding can be achieved either by direct condensation of existing side chains or by incorporation of external bridging molecules. Many bivalent or polyvalent linking agents are useful in coupling protein molecules, such as a carrier, to other molecules. Representative coupling agents include organic compounds such as thioesters, carbodiimides, N-hydroxysuccinimide esters, diisocyanates, glutaraldehyde, diazobenzenes, and hexamethylene diamines. It is understood that this listing is not an exhaustive compilation of the various classes of coupling agents known in the art but, rather, is representative of the more common coupling agents.

Illustrative everolimus immunoassays employ anti-everolimus antibodies that can be either polyclonal or monoclonal. In illustrative competitive immunoassays, the antibody preparation used is induced by an immunogen described herein is formulated in an aqueous solution such as buffer, and the like or provided in an adjuvant or similar composition. The induced antibodies can be tested to determine specificity for everolimus.

EXAMPLE I

Synthesis of Immunogenic Compounds and Labeled Competitors Synthesis of RAD-Mono-Formate 0.6 g of RAD was dissolved in 2 mL of dry methylene chloride in a 100 mL round bottom flask under an atmosphere of argon (Ar). An aliquot (~10 μL) was saved for HPLC and TLC assays. The round bottom flask containing the reaction solution was placed in the ice/NaCl bath at about −20° C. The reaction flask was allowed to cool down for 3–5 min. Dry pyridine (0.25 mL) was added using a dry glass syringe with a metal needle (15 cm) all at once. 0.35 mL dry allyl chloroformate was added using a dry glass syringe with a metal needle (15 cm) within about ½-1 min. Shortly after addition, precipitation occurred. The stirring was allowed for one hour. The reaction was quenched by adding 5 mL of saturated $NaHCO_3$. The quenched reaction was extracted with methylene chloride. The organic phase was combined, dried ($Na_2SO_4$) and filtered. The filtrate was transferred to a 250 ml bottom flask (100–250 mL) and the volatiles were evaporated under reduced pressure (water bath below +30° C.). The crude product was purified in silica chromatography in 40% ethyl acetate in methylene chloride. The final product was yielded 0.53 g.

Synthesis of Tethered-RAD-Formate (FIG. 1)

RAD-monoformate 0.4 g, DMAP 9 mg, pimelic acid mono allylester 0.2 g were placed in a dry 50 mL round bottom flask equipped with a stir bar. 5 mL of dry $CH_2Cl_2$ was added to the above flask that is placed in an ice/water bath at 0° C. under Argon. The solution was allowed to cool for 5–10 min. DCC 0.2 g was added quickly. The reaction was allowed to stir for five hours at 0° C. The precipitated DCU was collected on a Whatman #1 filter. The flask and precipitate were rinsed with about 10 mL of ice cold $CH_2Cl_2$ combined, and the organic layer was washed with ice cold 1M HCl, saturated aqueous sodium bicarbonate, dried over $Na_2SO_4$, decanted (or filtered), the solid rinsed with 2×5 mL $CH_2Cl_2$, and the crude product concentrated under vacuum yielding 0.45 g. Further purification can be achieved by flash chromatography on silica gel column in ethyl acetate/methylene chroloride (1:1).

Figure 2:
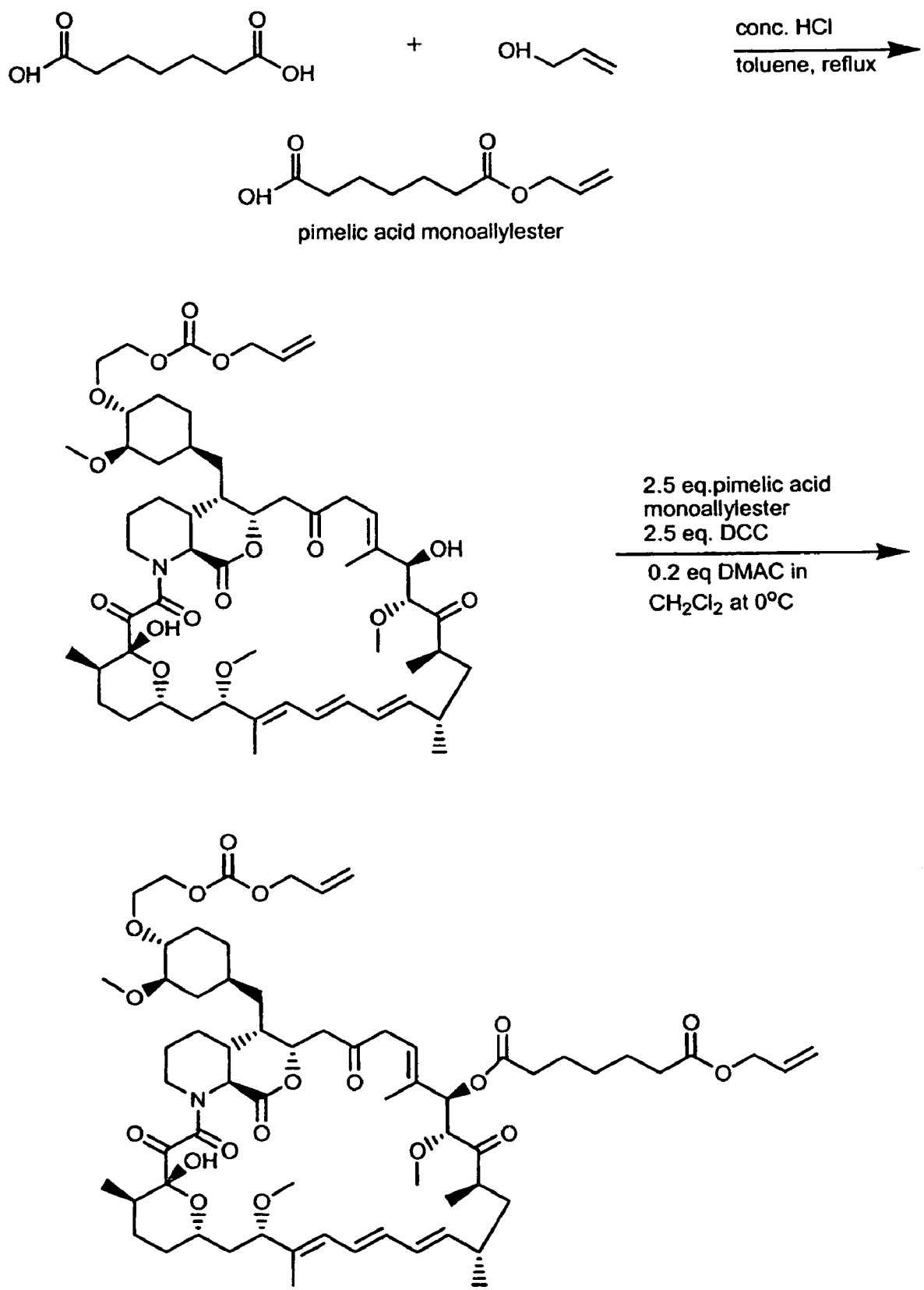
FIG. 2 shows synthesis of tethered-RAD-formate.

Synthesis of RAD-Acid (Deprotection) (FIG. 2)

0.362 g of protected RAD was placed under argon in dry amber round bottom flask equipped with a stir bar and a rubber seal at room temperature. The reagents were allowed to warm for at least 30-min at room temperature to protect from moisture condensation. 5.75 mL of dry methylene chloride was added into the reaction flask using a dry syringe (plastic or glass) with a dry needle and 73 μL (4 equivalents) of glacial acetic acid was added using an automatic pipette. Tetrakis-(triphenylphosphine)-palladium(0) ($Pd(PPh_3)_4$) 7.4 mg (0.02 equivalent or 2%) was weighted out on a weighing paper and added to the reaction solution. 260 μL of Tributyltin hydride was added drop-wise to the above reaction mixtures at room temperature. The reaction was allowed to stir for about 30 min at room temperature. The flask was placed on a rotary evaporator and condensed the content to about 2–3 mL solution. The solution was loaded on a short 5–6 cm glass chromatography column (dry $SiO_2$ volume=50 $cm^3$, diameter about 4 cm). Elute: $1^{st}$-200 mL ethyl acetate, $2^{nd}$-200 mL 10% acetone in ethyl acetate, $3^{rd}$-200 mL 50% acetone in ethyl acetate, pure acetone about 1.5 L. The product fractions were collected and concentrated under vacuum yielding 273 mg of RAD acid.

Figure 3:
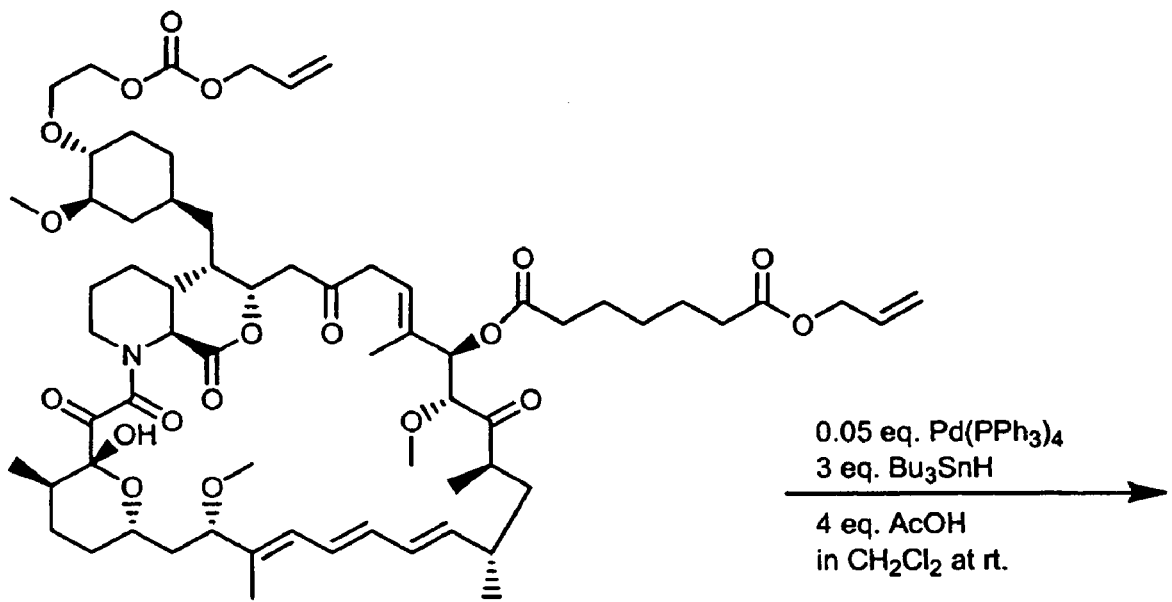
FIG. 3 shows synthesis of RAD-acid (deprotection)
Figure 3:
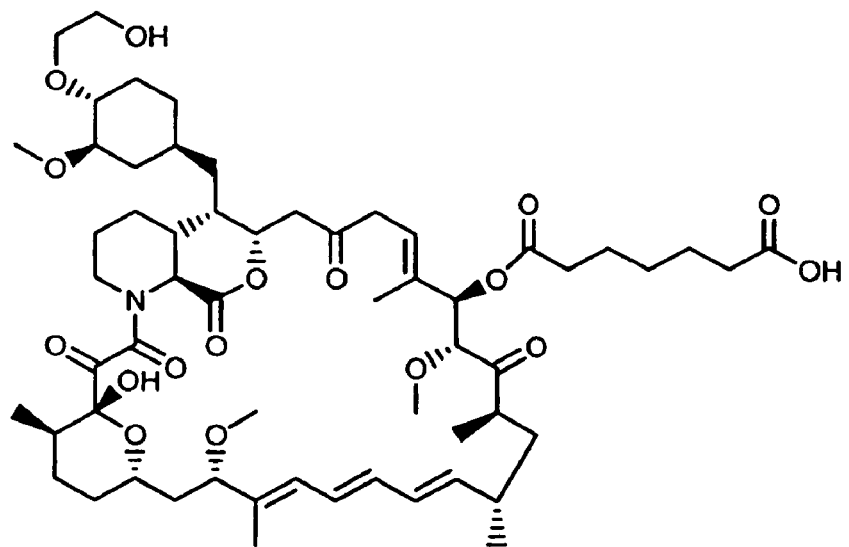

Synthesis of RAD-822 (NHS Activation) (FIG. 3)

RAD-acid 0.281 g obtained in the previous step was allowed to warm to room temperature and back filled with argon. DMAP 3.1 mg (0.1 equivalent), N-hydroxysuccinimide (NHS) 88 mg (3 equivalents), DCC 79 mg (1.5 equivalent) were added quickly into the reaction flask. The reaction was initiated by adding 3.0 mL of dry methylene chloride via syringe. The reaction was allowed to proceed at room temperature for 1 hr stirring under argon. The reaction was placed on an ice/water bath and allowed to stir for additional 2 hrs. At the end of this time 1.5 mL of hexane was added and stirring was stopped. The precipitated urea (DCU) was filtered through a cotton plug using a Pasteur pipette. The organic phase was extracted in sequence with equal volumes of ice cold 1.0M HCl, sat. NaCl, sat. $NaHCO_3$, sat. NaCl, distilled water. The organic phase was dried with $Na_2SO_4$, and concentrated under reduced pressure. The crude RAD-822 was dissolved in about 1 mL of $CH_2Cl_2$ and loaded on the silica gel column. The sample was eluted by hexane/acetone (1:1). The product was collected and concentrated under vacuum yielding 46 mg.

RAD-822 may be used in various embodiments of the present invention. This compound is used herein in an illustrative FPIA embodiment with an ester modified linker at position 28. However, RAD 822 can undergo chemical degradation via hydrolytic cleavage due to an elimination reaction. Thus, RAD 822 is not optimal for other embodiments requiring vigorous heat stressing conditions, such as QMS® technology (Seradyn, Indianapolis, Ind.).

Figure 4:
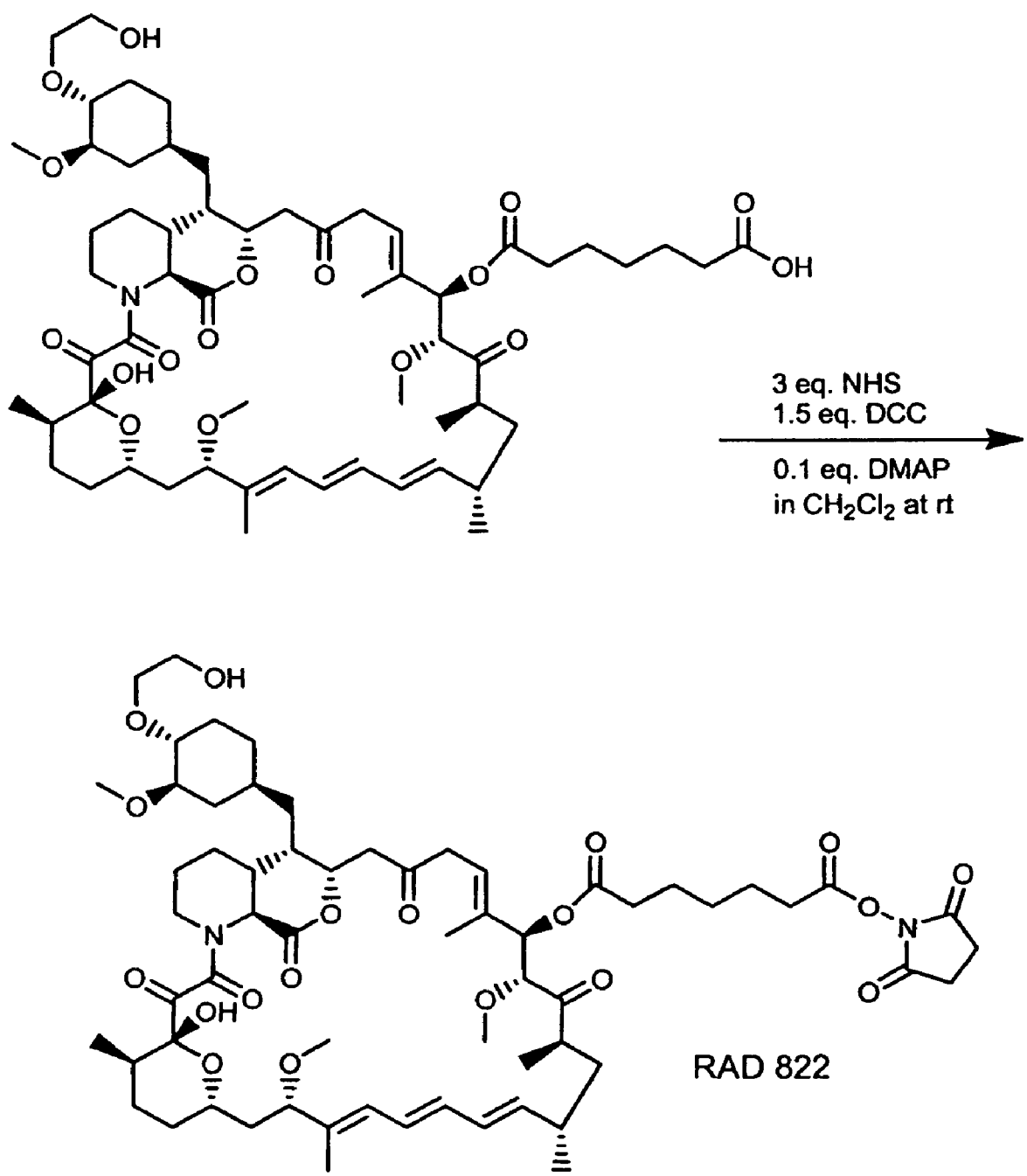
FIG. 4 shows synthesis of RAD-822 (NHS activation)

Synthesis of RAD 822: FAMCO-E FP Tracer (FIG. 4)

A 100 ml round bottom flask was weighed and 1 ml solution of FAMCO-E solution was pipetted into a suitable sized round bottom flask. The solvent was rotavapored off under reduced pressure. The flask with plastic cap was wrapped around with aluminum foil and a magnetic stirrer was added to the above flask. 1 ml DMF solution was pipetted into the flask above and stirred at room temperature for 40–50 minutes. A sufficient quantity of RAD was removed from −78° C. freezer storage and placed at room temperature to thaw. 4 mg of RAD 822 was weighed onto a piece of weighing paper and the powder transferred to the flask containing FAMCO-E solution. The reaction was allowed to stir under Argon pressure on the magnetic stir plate for 1 hr in an ice/water bath and then 30–40 minutes at room temperature (no more than 2 hours total). The solvent was evaporated under reduced pressure (high vacuum pump). The crude product (0.5–2 ml for a 1 mg batch size) was dissolved in minimal amount of methanol. TLC Solvent was prepared by adding 85 ml $CH_2CL_2$ and 15 ml MeOH. The plates were allowed to air dry for at least 60 minutes in an operating fume hood, and the tracer band was scraped from the plate. The powder was transferred to a 30 ml (porosity M) Buchner filter funnel and washed with 100% methanol. Filtrate was collected and transferred to a suitable sized round bottom flask. The filtrate was concentrated to dryness and re-dissolved in methanol. The solution was filtered through a 0.45 μm filter and the filtrate was collected in the amber vessel.

Synthesis of RAD 822: BSA Immunogen (FIG. 5)

In a 100 ml round bottom flask equipped with a teflon-coated magnetic stir bar, the DMSO (6.8 ml) solution of RAD 822 (27.2 mg) was added slowly drop wise to BSA: PBS (10 ml, 20 mM PBS pH 7.2) solution under vigorous stirring conditions at room temperature. The solution started turning cloudy gradually. The round bottom flask was covered with aluminum foil and allowed to stir for another 2 hours at room temperature, then it was dialyzed in a snake skin dialysis tube (Pierce) against 50 mM PBS buffer pH 7.5 in a cold room five times. Final volume was 45 mL. The solution was concentrated to 9 mL(~8 mg/mL) using Amicon Centriprep concentrator(Lot 874710, 10 kD MWCO). The solution was mixed well to assure homogeneity.

Synthesis of Everolimus-O-Carboxymethyl-32-Oxime (FIG. 6)

To a solution of everolimus, 290 mg in 3.0 mL of dry pyridine at +23° C., was added 160 mg of carboxymethoxylamine hemihydrochloride. The reaction was conducted under an inert atmosphere in a round bottom flask equipped with a stir bar. After stirring the reaction solution for 5–6 hours, the content was diluted with ~25 mL of methylene chloride and extracted successively with equal volumes of 1.2 M cold HCl, saturated sodium bicarbonate, and saturated sodium chloride. The resulting organic phase was dried with anhydrous sodium sulfate, concentrated under vacuum and used in the next activation step as is.

HPLC analysis on "Silica" stationary phase (from Regis Technologies) using 4% methanol, 40% ethyl acetate in hexane as a mobile phase at 2 ml/min (UV detection at 280 nm) indicates that the reaction leads to formation of isomers (E and Z), and the ratio is 3:1 (assuming similar extinction coefficients). Exact Mol Mass: 1030.6. MS-ESI (M+Na$^+$): 1052.8.

Synthesis of an Activated Ester (Succinimide) of Everolimus-O-carboxymethyl-32-Oxime (FIG. 7)

Dry N,N-dimethylamino pyridine (DMAP) 7 mg, dicyclohexylcarbodiimide (DCC) 124 mg, N-hydroxysuccinimide (NHS) 173 mg and Everolimus-O-carboxymethyl-27-oxime 309 mg (from the previous step) all were mixed together dissolved in dry methylene chloride and chilled to 0° C. After stirring for about 6 hours under inert atmosphere, the resulting suspension was filtered and extracted consecutively with 1.2 M HCl, saturated sodium bicarbonate, and saturated sodium chloride. The resulting organic phase was dried with anhydrous sodium sulfate and chromatographed on silica gel using successively the following solvent mixtures: hexane/acetone (3/2), hexane/acetone (1/1), hexane/acetone (2/3) all v/v. Major product-containing fractions were combined and concentrated under vacuum yielding 116 mg of the activated ester.

HPLC analysis on "Silica" stationary phase (from Regis Technologies) using 4% methanol, 40% ethyl acetate in hexane as a mobile phase at 2 ml/min (UV detection at 280 nm) indicates that the reaction leads to formation of E and Z isomers (no base line resolution). Thin layer chromatography in mixture of acetone/hexane (3/2, v/v): Rf=0.48.

Exact Mol Mass: 1127.6. MS-ESI (M+Na$^+$): 1150.6.

Figure 8:
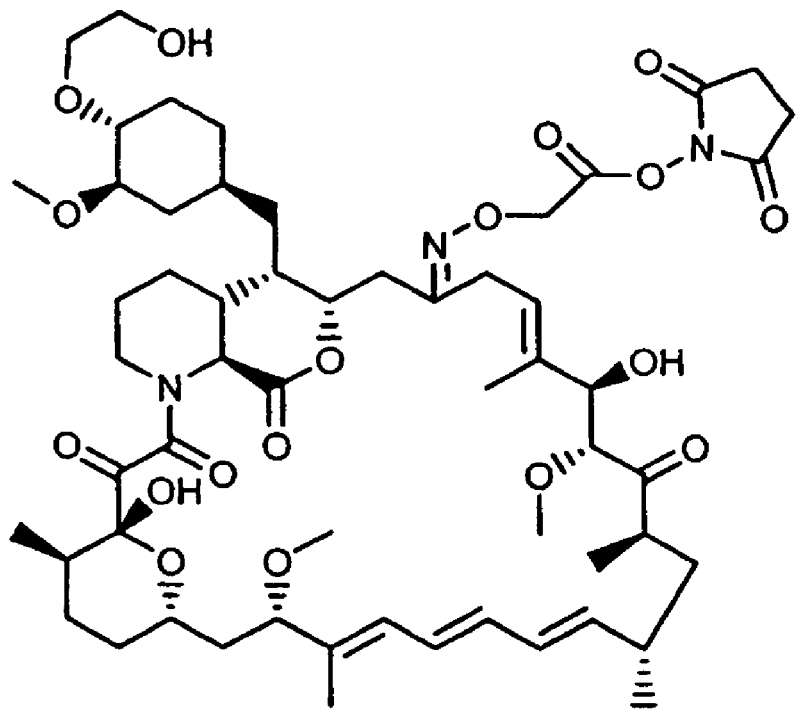
FIG. 8 shows an activated ester of the 32-oxime derivative of FIG. 8.

The resulting compound is shown in FIG. 8. It is understood that the succinimide group may be replaced with an immunogen, similar to the process described above with RAD 822 to obtain RAD 822:BSA, or the succinimide group may be replaced with a label, similar to the process described above with RAD 822 to obtain RAD 822: FAMCO-E. It is understood that other immunogens, labels, and tracers may be used.

EXAMPLE II

Antibody Preparation

Polyclonal anti-everolimus antibodies can be prepared by conventional methods. Animals were immunized with everolimus immunogen (RAD 822/BSA), as produced in Example I. The immunization program started with initial injection of 0.5 ml immunogen mixing with 0.5 complete Freunds adjuvant. Subsequent injections were performed with 0.5 ml immunogen mixing with 0.5 incomplete Freunds adjuvant. Animals were typically injected every two weeks. Sera were screened via FPIA using RAD 822: FAMCO-E tracer. Several bimonthly production bleeds (~20 mL per bleed) from three rabbits were pooled together. Before filter and dilution, the total pooled volume is about 500 mL. Anti-Sera from Rabbit were filtered with 0.2 um Cellulose Acetate Filter under vacuum and diluted with phosphate buffer with sodium azide and sodium chloride at pH 7.5. The final volume is about 1000 ml.

Monoclonal anti-everolimus antibodies can be prepared by immunization of mice. A mouse can be injected with a composition containing an immunogen of this invention and Freund's adjuvant. After the last immunization, the mouse was killed and spleen was processed. The spleen cells were fused with myeloma cells. The fused cells were allowed to grow and supernatant was screened via ELISA.

EXAMPLE III

Fluorescence Polarization Immunoassay using RAD 822: FAMCO-E Tracer

Automated Fluorescence Polarization Immunoassay (FPIA).

This example describes an exemplary fluorescence polarization immunoassay (FPIA) for everolimus.

The fluorescence polarization immunoassay was performed using an automated TDx polarization analyzer (Abbott Laboratories, Irving, Tex.) using a competitive assay included anti-analyte antibody (the anti-everolimus antibody of Example II) or "A", a fluorescein:everolimus analog conjugate (tracer or "T"), and a pretreatment buffer or "B." The calibration of the automated assay described in the examples was achieved with a series of six calibrators that include specified concentrations of everolimus spiked into human serum. Patient samples (plasma) are placed in plastic sample cups in a circular carousel designed for the TDx instrument. The automated assay is described in detail in literature available from Abbott Laboratories, Irving, Tex. It is understood that, while the TDx polarization analyzer is used in this example, other devices may be used to detect the polarization in an FPIA.

Specimen Collection and Preparation for Analysis

This assay has only been characterized for trough samples.

Whole blood treated with EDTA is used for each assay. Each assay uses 600 µl of whole blood, collected using normal aseptic venipuncture technique in glass or plastic EDTA tubes. Illustratively, patient samples can be stored at 2–8° C. for up to 24 hours. If longer storage is required, whole blood may be frozen at −20° C. or colder and can be tested up to 28 days later. Illustratively, frozen samples are thawed completely and mixed thoroughly prior to use. All samples (frozen and fresh) are mixed thoroughly by gently inverting multiple times prior to performing the sample extraction.

Reagents

Antibody Reagent (5 mL)—<5% rabbit antisera in buffer containing protein as stabilizer and <0.1% sodium azide as preservative. The polyclonal Antibody Reagent was produced in methods consistent with Example II, using the immunogen shown in FIG. 6 (RAD 822:BSA).

Tracer Reagent (5 mL)—<1% fluorescein tracer (RAD 822: FAMCO-E FP, as shown in FIG. 5) in buffer containing 0.01 M PBS, pH 7.5, 0.1% sodium azide, and 0.01 mg/ml bovine gamma globulin. Vial cap labeled "T".

Pretreatment Buffer (5 mL)—tris buffer, detergent, and <0.1% sodium azide as preservative. Vial cap labeled "B".

Precipitation Reagent (7.5 mL)—containing precipitating reagent and <0.1% sodium azide.

Assay Procedure

A. Sample Extraction Procedure:

Samples (calibrators, patient samples, and controls) are extracted just prior to analysis by the instrument. 600 µl of each calibrator, control, or sample to be assayed is pipetted into the appropriate centrifuge tube. 700 µl of methanol is dispensed to the sample and 100 µl of Precipitation Reagent is added into each centrifuge tube containing sample and methanol. Each centrifuge tube is capped immediately to prevent evaporation, then mixed/vortexed vigorously at the highest speed for at least 10 seconds, and centrifuged for at least 8 minutes at 13,400×g. After centrifuging, at least 300 µl of each supernatant is pipetted into sample cartridges loaded into the carousel and the instrument is started immediately, to minimize sample evaporation.

B. Summary of Procedure:

Two cartridges and 2 cuvettes for each patient sample and control are placed into an assay carousel. At least 300 µl of the supernatant from Sample Extraction Procedure is pipetted into each sample well, avoiding bubbles. The reagents are mixed by gentle inversion. The vial caps are removed and the reagent set and the assay carousel are placed in the analyzer and the assay process started without delay.

The reference material used was prepared by gravimetric addition to human blood hemolysate. Each lot of calibrator is value assigned on the TDx® using a reference material that is traceable to a validated LC/MS method. As currently configured, the assigned value concentration of each level of calibrator is printed on the calibrator carton label and enclosed calibrator value card. These values are programmed into the TDx® parameters with each new lot of calibrator. The assay range is from 2.00 ng/mL to the assigned value of the F calibrator (~40 ng/mL).

Results

The illustrative assay system is a quantitative procedure. Everolimus concentrations are recorded on the TDx®/TDx-Flx® analyzer printout in ng/mL. Patient sample results lower than the sensitivity of the assay should be reported as "<2.00 ng/mL". The everolimus concentration in most samples will fall within the assay range. If the value from a patient sample is greater than the F calibrator, "HI" will be printed. Illustratively, such samples may be manually diluted (1:1 or 1:4) with whole blood negative for everolimus, re-assayed by perform the sample extraction procedure, and the final printed value multiplied by the dilution factor to obtain the true concentration.

It is preferred that calibrators, controls, and samples should be run in replicates of two or greater and the mean value reported. It is preferred that results with a coefficient of variation (CV) of duplicates greater than 20% be repeated.

The majority of the sample extract is methanol. Due to the volatility of methanol, the time between extraction and sample analysis has been limited to prevent evaporation. Evaporation of the samples may lead to falsely elevated results. Accordingly, if samples are loaded onto the instrument and the run is aborted, these samples have been re-extracted and re-run.

C. Performance Characteristics of the FPIA using polyclonal Antibody Reagent (RAD 822:BSA) and Tracer Reagent (RAD 822:FAMCO-E)

1. Recovery of Spiked Samples

Whole blood specimens negative for everolimus were spiked with everolimus across the assay range then assayed n=3 on three different analyzers. The mean value was compared to LC/MS value, and percent recovery calculated. The results are shown in Table 1.

TABLE 1

Percent recovery = mean TDx result ÷ LC/MS result × 100%

| TDx Avg TDx Result (ng/mL) | LC/MS Avg LC/MS Result (ng/mL) | Percent Recovery |
|---|---|---|
| 32.07 | 39.53 | 81% |
| 22.32 | 28.46 | 78% |
| 14.52 | 17.39 | 83% |
| 7.27 | 9.49 | 77% |
| 3.63 | 4.74 | 77% |

2. Patient Sample Correlation to Reference Method

Figure 10:
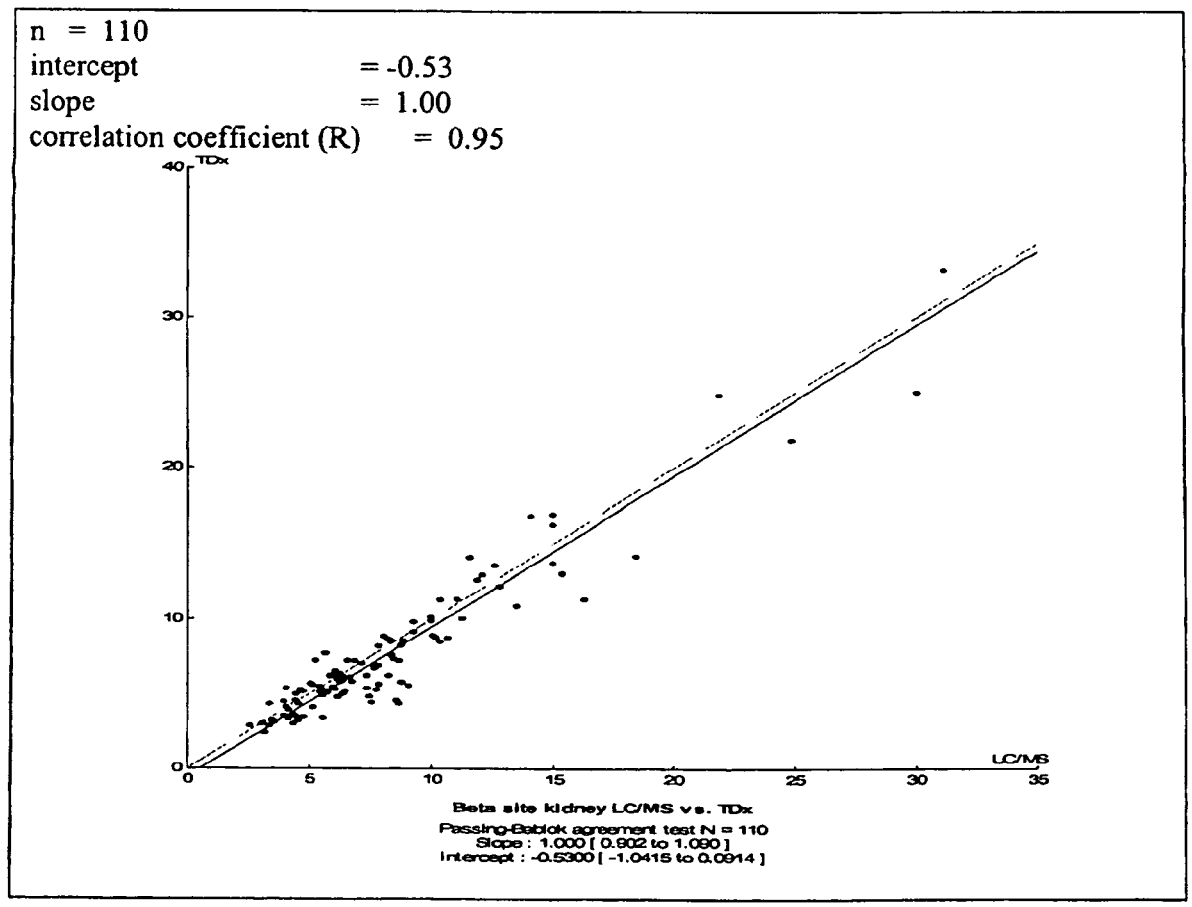
FIG. 10 shows a comparison of an everolimus FPIA assay according to the present invention vs. LC/MS in kidney transplant patients.
Figure 11:
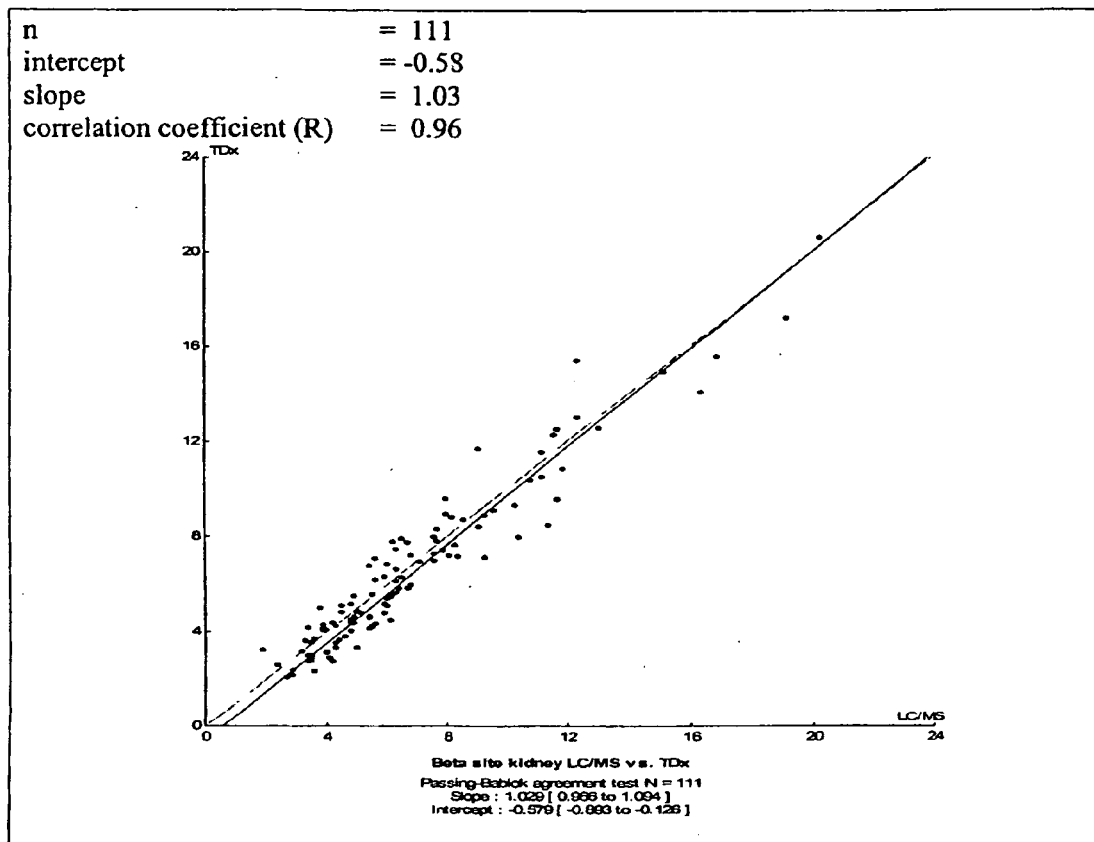
FIG. 11 shows a comparison of an everolimus FPIA assay according to the present invention vs. LC/MS in heart transplant patients.
Figure 12:
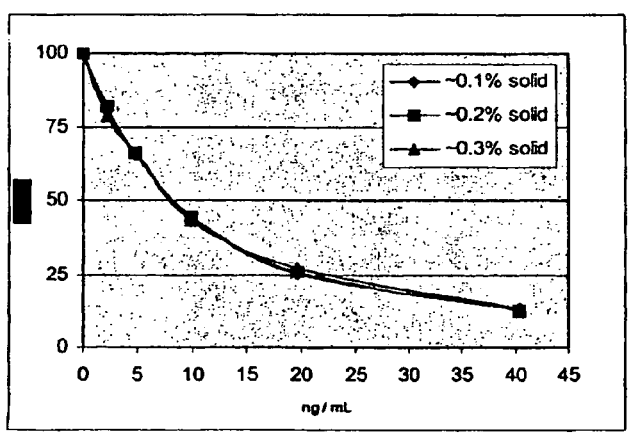
FIG. 12 is an everolimus QMS calibration curve (antibody: polyclonal antibody from RAD 822 immunogen; antigen: Oxime (FIG. 5) derivative coupled to the particles.

Concentrations measured by the illustrative assay system on the TDx® were compared with those measured by LC/MS on whole blood samples from patients receiving everolimus therapy. Results of testing from two reference laboratories are shown in FIG. 10 for kidney transplant patients (data analyzed using Passing Bablock Linear Regression Analysis), comparing the illustrative assay system vs. LC/MS. Samples ranged on the TDx from 2.40 ng/mL to 33.17 ng/mL and are from 110 individual patients. Similarly, results of testing from two reference laboratories are shown in FIG. 11 for heart transplant patients (data analyzed using Passing Bablock Linear Regression Analysis), comparing the illustrative assay system vs. LC/MS. Samples ranged on the TDx from 2.06 ng/mL to 20.60 ng/mL and are from 62 different individual patients. The illustrative assay system shows a linear relationship between percent dilution and recovery across the assay range.

Precision of the illustrative assay system was evaluated per NCCLS guidelines. Studies were performed by assaying each sample in duplicate, two runs per day for 20 non-consecutive days on a single analyzer, and calibrating as needed. The results are shown below in Table 2.

TABLE 2

| | Precision study | | |
|---|---|---|---|
| | Level 1 | Level 2 | Level 3 |
| Mean (ng/mL) | 3.28 | 12.38 | 36.55 |
| Within Run SD (ng/mL) | 0.35 | 0.73 | 3.13 |

TABLE 2-continued

Precision study

| | Level 1 | Level 2 | Level 3 |
|---|---|---|---|
| Within Run % CV | 11% | 6% | 9% |
| Day to Day SD (ng/mL) | 0.39 | 0.63 | 1.85 |
| Day to Day % CV | 12% | 5% | 5% |
| Run to Run SD (ng/mL) | 0.35 | 0.66 | 1.74 |
| Run to Run % CV | 11% | 5% | 5% |
| Total SD (ng/mL) | 0.63 | 1.17 | 4.03 |
| Total % CV | 19% | 9% | 11% |

3. Specificity—Cross-Reactivity

Studies were conducted to examine the cross-reactivity of the Antibody Reagent "A" to major everolimus metabolites. The compounds (in Table 3 below) were added at 5 ng/mL to normal pooled human whole blood (containing everolimus spiked at the low end of the therapeutic range, approximately 4 ng/mL) and tested in the illustrative assay system. The normal human whole blood spiked with everolimus was tested as the control.

Although tested at 5 ng/mL, lower metabolite concentrations would be expected in actual patients on everolimus therapy. RAD SA, RAD and PSA have been found in quantities <20% of parent drug in drug metabolism studies of human subjects. The Hydroxyl-(24/25 OH RAD, 46OH RAD) metabolites cross reactivity were not tested by spiked addition.

TABLE 3

Cross-reactivity: % cross-reactivity = ([measured everolimus with spiked metabolite] − [measured control] ÷ [metabolite added]) × 100

| Compound Tested | Concentration Tested (ng/mL) | Apparent Conc. (ng/mL) | % Cross reactivity |
|---|---|---|---|
| RAD SA | 5 | 0.26 | 5 |
| RAD PSA | 5 | 0.62 | 12 |

4. Specificity—Drug Interference

The illustrative assay system was tested against potentially interfering compounds. The substances shown in Table 4, when added to human whole blood (containing 12 ng/mL everolimus), had cross reactivity less than 5% when tested at concentrations exceeding clinically relevant levels.

TABLE 4

Drug Interference

| Drug | Test Level (μg/mL) |
|---|---|
| Acetaminophen | 200 |
| N-Acetylprocainamide | 120 |
| Acyclovir | 1000 |
| Albuterol | 0.18 |
| Allopurinol | 60 |
| Amikacin | 150 |
| Amphotericin B | 100 |
| Ascorbic Acid | 30 |
| Atenolol | 40 |
| Azathioprine | 10 |
| Caffeine | 100 |
| Captopril | 50 |
| Carbamazepine | 120 |
| Cefaclor | 230 |
| Chloramphenicol | 250 |
| Cimetidine | 100 |
| Ciprofloxacin | 2500 |
| Cyclosporin A | 1 |
| Digoxin | 10 |
| Disopyramide | 30 |
| Erythromycin | 200 |
| Ethanol | 3500 |
| Folic Acid | 0.01 |
| Furosemide | 100 |
| Ganciclovir | 1000 |
| Gentamicin | 20 |
| Glipzide | 60 |
| Glyburide | 40 |
| Heparin | 8000 U/L |
| Hydralazine | 32 |
| Hydrochlorothiazide | 40 |
| Ibuprofen | 400 |
| Insulin | 400 μU/mL |
| Intralipid | 15000 |
| Isoniazid | 70 |
| Isoproternol Hydrochloride | 0.06 |
| Kanamycin | 100 |
| Ketoconazole | 10 |
| Labetalol | 200 |
| Lidocaine | 100 |
| Lovastatin | 4 |
| Metformin HCl | 5100 |
| Metoclopramide | 4 |
| Misoprostol | 0.015 |
| Morphine Sulfate | 6 |
| Mycophenolic Acid | 250 |
| Nadolol | 333 |
| Naproxen | 1000 |
| Niacin | 800 |
| Nifedipine | 120 |
| Omeprazole | 14 |
| Penicillin G | 100 |
| Phenobarbital | 150 |
| Phenytoin | 100 |
| Piperacillin | 8 |
| Prazosin | 25 |
| Prednisone | 12 |
| Prednisolone | 12 |
| Primidone | 100 |
| Procainamide | 25 |
| Propanolol | 0.5 |
| Quinidine | 100 |
| Ranitidine | 200 |
| Rifampin | 50 |
| Salicylic Acid | 500 |
| Spectinomycin | 100 |
| Sulfamethoxazole | 400 |
| Tacrolimus | 0.5 |
| Theophyline | 250 |
| Tobramycin | 20 |
| Triamterene | 600 |
| Trimethoprim | 20 |
| Valproic Acid | 1000 |
| Vancomycin | 630 |
| Verapamil | 10 |

Specificity—Interfering Substances

The following compounds, as shown in Table 5, when added to normal human whole blood containing everolimus at or below the low end of the therapeutic range resulted in ≦10% error in quantitating everolimus by the illustrative assay system.

TABLE 5

| Interfering Substances | |
| --- | --- |
| Compound Tested | Concentration Tested |
| Albumin | 12 g/dL |
| Bilirubin | 20 mg/dL |
| Cholesterol | 500 mg/dL |
| Human Gamma Globulin | 12 g/dL |
| Rheumatoid Factor | 500 IU/mL |
| Triglycerides | 1,500 mg/dL |

Hematocrits at 20% and 60%, resulted in ≦10% error in quantitating everolimus by the illustrative assay system.

5. Sensitivity

The Limit of Quantification (LOQ) of the illustrative assay system, defined as the lowest concentration in human whole blood at which inter-assay CV between multiple replicates is ≦20%, is 2.00 ng/mL.

The lower limit of detection (LDD) for the illustrative assay system, defined as the lowest concentration that can be distinguished from zero, is 0.80 ng/mL.

It is understood that the above results are illustrative of one embodiment of FPIA using polyclonal Antibody Reagent (RAD 822:BSA) and Tracer Reagent (RAD 822:FAMCO-E). Other competitive assays within the scope of this invention may provide different performance characteristics.

All references cited herein are incorporated by reference as if fully set forth.

Although the invention has been described in detail with reference to preferred embodiments, variations and modifications exist within the scope and spirit of the invention as described and defined in the following claims.

The invention claimed is:

1. A method of determining the concentration of everolimus in a sample, said method comprising the steps of:
    (a) providing a labeled competitor comprising everolimus coupled to a detectable label through an oxime linkage;
    (b) providing an anti-everolimus antibody produced by using an antigenic compound comprising everolimus coupled to an antigenic carrier through a linker having a different structure or position than said oxime linkage;
    (c) combining said sample, said anti-everolimus antibody and said labeled competitor, the everolimus in said sample competing with said labeled competitor for binding to said anti-everolimus antibody; and
    (d) determining the concentration of everolimus in said sample by measuring the amount of said labeled competitor not bound to said antibody by detection of said label.

2. The method of claim 1, wherein said antigenic compound comprises everolimus coupled to an antigenic carrier through a linker at a position selected from the group consisting of the 26 and 28 positions.

3. The method of claim 1, wherein said labeled competitor has the formula:

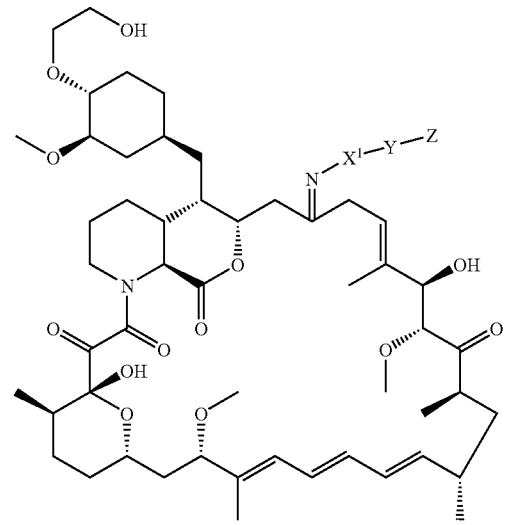

and wherein
  $X^1$ is a linker chain comprising one or more atoms including oxygen, each of which may be substituted or unsubstituted and may be branched or unbranched, wherein the oxygen is linked to nitrogen;
  Y is selected from the group consisting of —C(O)—, —NH—, —S—, —CH$_2$— and —O—; and
  Z is said detectable label.

4. The method of claim 1 or claim 3, wherein said antigenic compound has the formula:

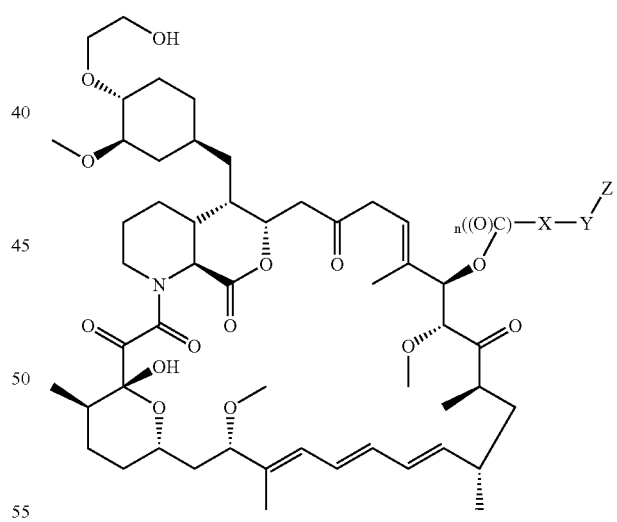

and wherein
  n is 0 or 1;
  X is a linker chain, wherein said linker chain may be substituted or unsubstituted and may be straight or branched;
  Y is selected from the group consisting of —C(O)—, —NH—, —S—, —CH$_2$— and —O—; and
  Z is said antigenic carrier.

5. The method of claim 4, wherein X is —CH$_2$—CH$_2$—CH$_2$—CH$_2$—CH$_2$— and Y is —C(O)—.

6. The method of claim 1, wherein said anti-everolimus antibody has a greater affinity for everolimus in said sample than for said labeled competitor.

7. The method of claim 1, wherein said step (d) of determining the amount of said labeled competitor not bound to said anti-everolimus antibody is performed by an automated assay selected from the group consisting of: FPIA, homogeneous microparticle (immunoturbidimetric) immunoassay, cloned enzyme donor immunoassay (CEDIA), chemiluminescent heterogeneous immunoassay, and lateral flow immunoassay.

8. A kit for determining the concentration of everolimus in a sample, said kit comprising:
   a labeled competitor comprising everolimus coupled to a detectable label through an oxime linkage; and
   an anti-everolimus antibody;
   wherein said anti-everolimus antibody is produced using an antigenic compound comprising everolimus coupled to an antigenic carrier through a linker having a different structure or position than said oxime linkage; and
   wherein said labeled competitor competes with said everolimus in said sample for binding to said anti-everolimus antibody.

9. The kit of claim 8, wherein said antigenic compound comprises everolimus coupled to an antigenic carrier through a linker at a position selected from the group consisting of the 26 and 28 positions.

10. The kit of claim 8, wherein said labeled competitor has the formula:

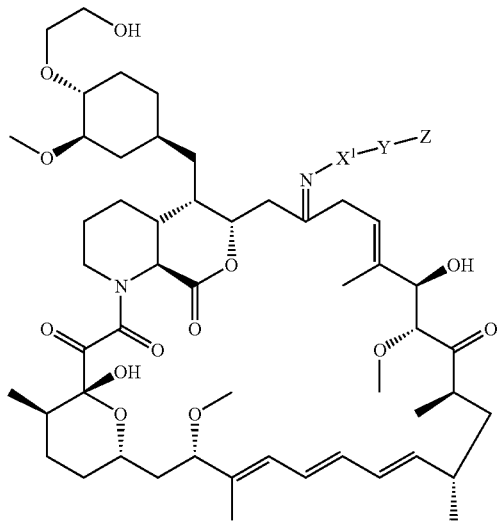

and wherein $X^1$ is a linker chain comprising one or more atoms including oxygen, each of which may be substituted or unsubstituted and may be branched or unbranched, wherein the oxygen is linked to nitrogen;

Y is selected from the group consisting of —C(O)—, —NH—, —S—, —CH$_2$— and —O—; and Z is said detectable label.

11. The kit of claim 8 or claim 10, wherein said antigenic compound has the formula:

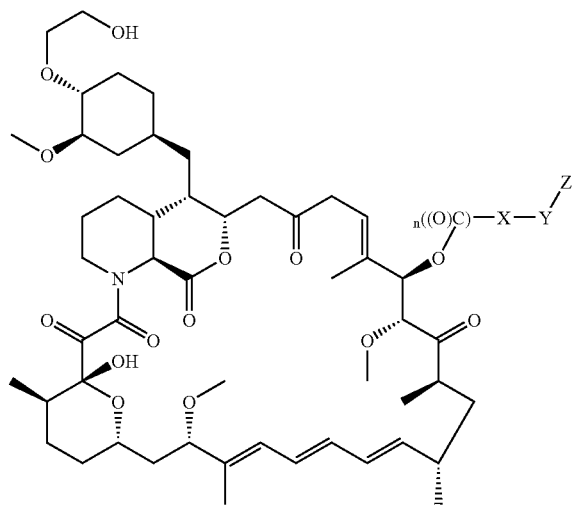

and wherein n is 0 or 1;

X is a linker chain, wherein said linker chain may be substituted or unsubstituted and may be straight or branched;

Y is selected from the group consisting of —C(O)—, —NH—, —S—, —CH$_2$— and —O—; and Z is said antigenic carrier.

12. The kit of claim 11, wherein X is —CH$_2$—CH$_2$—CH$_2$—CH$_2$—CH$_2$— and Y is —C(O)—.

13. The kit of claim 8, wherein said anti-everolimus antibody has greater affinity for said everolimus in said sample than for said labeled competitor.

14. The kit of claim 8, wherein said anti-everolimus antibody is a monoclonal antibody.

15. The kit of claim 8, wherein said anti-everolimus antibody is a polyclonal antibody.

16. The kit of claim 8, wherein said kit is sufficient to determine the concentration of everolimus in a sample in the range of about 3 ng/ml to about 15 ng/ml.

* * * * *